(12) United States Patent
Niwayama (10) Patent No.: US 8,338,635 B2
(45) Date of Patent: Dec. 25, 2012

(54) SYNTHESIS OF HALF ESTERS

(75) Inventor: Satomi Niwayama, Lubbock, TX (US)

(73) Assignee: Satomi Niwayama, Lubbock, TX (US)

( * ) Notice: Subject to any disclaimer, the term of this patent is extended or adjusted under 35 U.S.C. 154(b) by 693 days.

(21) Appl. No.: 12/156,448

(22) Filed: May 30, 2008

(65) Prior Publication Data

US 2009/0023945 A1     Jan. 22, 2009

Related U.S. Application Data (60) Provisional application No. 60/932,629, filed on May 31, 2007.

(51) Int. Cl.
*C07C 69/34* (2006.01)
*C07C 69/52* (2006.01)
*C07C 69/76* (2006.01)

(52) U.S. Cl. ............................. 560/190; 560/82; 560/120

(58) Field of Classification Search .................... 560/82, 560/120, 190
See application file for complete search history.

(56) References Cited

U.S. PATENT DOCUMENTS

| | | | |
|---|---|---|---|
| 3,150,165 A | 9/1964 | Chafetz | |
| 4,220,708 A | 9/1980 | Heller | |
| 4,254,111 A | 3/1981 | Pegel et al. | |
| 4,267,087 A | 5/1981 | Mueller | |
| 4,361,710 A | 11/1982 | Weitz et al. | |
| 4,460,512 A | 7/1984 | Millauer | |
| 4,728,466 A | 3/1988 | Young et al. | |
| 5,047,574 A | 9/1991 | Ohtani et al. | |
| 5,123,951 A | 6/1992 | See et al. | |
| 5,273,989 A | 12/1993 | Schwab et al. | |
| 5,302,305 A | 4/1994 | Jolley et al. | |
| 5,597,555 A | 1/1997 | Pereira et al. | |
| 5,928,909 A | 7/1999 | Prakash et al. | |
| 6,833,471 B2 | 12/2004 | Rozzell et al. | |
| 7,081,535 B2 | 7/2006 | Rozzell et al. | |
| 7,109,369 B2 * | 9/2006 | Nose et al. | 560/82 |
| 7,173,084 B2 | 2/2007 | Pirrung et al. | |
| 7,208,621 B2 | 4/2007 | Nose et al. | |
| 7,217,424 B2 | 5/2007 | Pereira et al. | |
| 7,301,031 B2 | 11/2007 | Rozzell, Jr. et al. | |
| 7,307,183 B2 | 12/2007 | Bartley et al. | |
| 2003/0199593 A1 | 10/2003 | Pereira et al. | |
| 2005/0004151 A1 | 1/2005 | Yang et al. | |
| 2005/0027139 A1 | 2/2005 | Bartley et al. | |
| 2007/0202069 A1 | 8/2007 | Tamareselvy et al. | |

OTHER PUBLICATIONS

Niwayama and Rimkus; "Effects of Counter Cations in Selective Monohydrolyses of Symmetric Diesters"; Bull. Chem. Soc. Jpn., 78, 498-500 (2005); 3 pages.

Niwayama, S.; "Highly Efficient Selective Monohydrolysis of Symmetric Diesters"; J. Org. Chemistry, 2000, 65, 5834-5836; 3 pages.

(Continued)

*Primary Examiner* — Yate K Cutliff (74) *Attorney, Agent, or Firm* — Fortkort & Houston P.C.; John A. Fortkort (57) ABSTRACT

A method for hydrolyzing an ester is provided. In accordance with the method, a compound A is provided which has first and second ester moieties. The compound is reacted in a liquid medium with a base having the formula $M_aX_b$, such that the first ester moiety is converted to a carboxyl moiety and the second ester moiety remains, wherein the ratio $[X^{k-}]$:[A] in the liquid medium is no greater than 1.6, and wherein $k>0$.

69 Claims, 2 Drawing Sheets

OTHER PUBLICATIONS

Niwayama, S. et al.; "Highly Efficient Selective Monohydrolysis of Dialkyl Malonates and Their Derivatives"; Dept. of Chem. and Biochem., Texas Tech Univ., 4 pages, Supporting information: 2000.

Niwayama, S., "Racemic novel buffer-mediated rearrangement"; Dept. of Chem., Oklahoma State Univ.; Tetrahedron Letters 41 (2000) 10163-10166.

Niwayama, S. "Influence of co-solvents in the highly efficient selective monohydrolysis of a symmetric diester"; Tetrahedron Letters 48 (2007) 8508-8510.

Niwayama, S. et al., "Highly efficient selective monohydrolysis of dialkyl malonates and their derivatives"; Dept. of Chem./Biochem.; Texas Tech University; Tetrahedron Letters; May 13, 2008; 3 pages.

Niwayama, Satomi; "Highly Efficient Selective Monohydrolysis of Symmetric Diesters"; 2000 American Chem. Society; J. Org. Chem. 2000, 65, 5834-5836; 3 pages.

Schmuck and Machon; "Amino Acid Binding by 2-(Guanidiniocarbonyl)pyridines in Aqueous Solvents: A Comparative Binding Study Correlating Complex Stability with Stereoelectronic Factors"; Chem. Eur. J. 2005, 11, 1109-1118; 10 pages.

Maruyama and Tamiaki; "Catalyticv Isomerization of Water-Soluble Quadricyclane to Norbornadiene Derivatives Induced by Cobalt-Porphyrin Complexes"; 1986 American Chemical Society; J. Org. Chem. 1986, 51, 602-606; 5 pages.

Search Report from corresponding PCT Application PCT/US08/06907; dated Nov. 12, 2008; 2 pages.

Niwayama, Satomi et al., "Influence of co-solvents in the highly efficient selective monohydrolysis of a symmetric diester"; Tetrahedron Letters 48 (2007) 8508-8510; Sep. 25, 2007; 3 pages.

* cited by examiner

FIG. 1

Time Dependence of Monohydrolysis

FIG. 2

SYNTHESIS OF HALF ESTERS

CROSS REFERENCE TO RELATED APPLICATIONS

This application claims the benefit of priority from U.S. Application No. 60/932,629 filed 31 May 2007, having the same title, and having the same inventor, and which is incorporated herein by reference in its entirety.

STATEMENT REGARDING FEDERAL SPONSORED RESEARCH OR DEVELOPMENT

This invention was prepared with the assistance of the National Science Foundation through Contract Number CHE-0443265. The government may have rights to this invention.

FIELD OF THE DISCLOSURE

The present disclosure relates generally to the chemical synthesis of esters, and more particularly to the synthesis of half esters from diesters.

BACKGROUND OF THE DISCLOSURE

Half esters are highly versatile building blocks in chemical synthesis, where they provide useful intermediaries to a wide variety of end products. Half esters themselves may be conveniently produced by the selective monohydrolysis of symmetric diesters. Since many symmetric diesters may be readily prepared from inexpensive sources or are commercially available in a variety of grades at commodity prices, synthetic routes based on half ester intermediates provide the additional advantages of economy and versatility.

Saponification or alkaline hydrolysis are both established methods for producing half esters from diesters. However, the application of these approaches to the formation of half esters from symmetric diesters is complicated by the difficulty in chemically distinguishing between the two identical functional groups in the starting diester. Consequently, this approach typically results in a complex mixture of dicarboxylic acids, monocarboxylic acids, and the starting diester. Aside from the obvious yield loss attendant to the formation of dicarboxylic acids and other reaction byproducts, the target half ester is difficult to separate from these reaction byproducts, due to their chemical similarity. Indeed, until recently, the only effective method reported in the literature for the synthesis of half esters from symmetrical diesters involved the use of enzymes. However, such a synthetic route is undesirable in that, among other things, it provides no basis for predictions of reactivity.

More recently, a new synthetic route has been disclosed for the production of half esters from symmetric diesters. This route, which involves the selective hydrolysis and subsequent acidification of the diester, affords the half ester in relatively high yields in a solution that is relatively free of byproducts (see S. Niwayama, "Highly Efficient Selective Monohydrolysis of Symmetric Diesters", *J. Org. Chem.* 2000, p 5834). This approach is summarized in SCHEME 1 below:

SUMMARY OF THE DISCLOSURE

In one aspect, a method is provided for hydrolyzing diesters or polyesters to produce half esters or other compounds having both carboxyl and ester moieties. In accordance with the method, a compound A is provided which has first and second ester moieties. The compound A is reacted in a liquid medium with a base having the formula $M_aX_b$, such that the first ester moiety is converted to a carboxyl moiety and the second ester moiety remains, wherein the ratio $[X^{k-}]$:[A] in the liquid medium or the number of equivalents of X to A is no greater than 1.6, and wherein k>0, where k is the valency of anion X.

In another aspect, a method for hydrolyzing an ester is provided which comprises providing a compound having first and second ester moieties, and reacting the compound with a base such that the ratio of the number of molar equivalents of base to the number of molar equivalents of the compound is no greater than 1.6.

In a further aspect, a method for hydrolyzing an ester is provided which comprises providing a compound having first and second ester moieties, and reacting the compound with a base in an aqueous medium comprising greater than 93% water by volume.

In yet another aspect, a method for hydrolyzing an ester is provided which comprises (a) providing a first compound having first and second ester moieties; (b) reacting the compound with a base in an aqueous medium such that the ratio of the number of molar equivalents of base to the number of molar equivalents of the first compound is greater than 3; and (c) quenching the reaction such that the total reaction time is no greater than 90 minutes.

DETAILED DESCRIPTION

While the approach summarized in SCHEME 1 is a highly efficient route for producing a variety of half esters from symmetric diesters, it has been found that this approach, as implemented in the above noted reference, produces sub-optimal yields for certain half esters. For example, while the aforementioned reference reports a yield of greater than 99% for the production of the half ester of bicycloheptadiene dimethylcarboxylate and bicycloheptadiene diethylcarboxylate, the reference reports a yield of the monoester formed by the monohydrolysis of dimethyl succinate of only 70%. Far lower yields are obtained when the approach, as implemented in the above noted reference, is applied to the synthesis of certain other half esters, such as monomethyl malonate malonate, where the yield is only 22%.

It has now been found that the yield of certain monoesters in the foregoing synthetic route may be significantly increased by adjusting the ratio of starting diester to base in the reaction solution and, in particular, by increasing the ratio of the number of equivalents (or concentration) of starting diester to the number of equivalents (or concentration) of base in the solution. Thus, for example, by using this approach, monomethyl malonate, the corresponding half ester of dimethyl malonate, has been obtained in substantially higher yields (84% in THF and 85% in acetonitrile) than those afforded by the approach summarized in SCHEME 1. It is expected that these yields may be even further improved by parameter optimization.

It has also been found that, in some cases, the synthetic methodologies taught herein may achieve the target compound in a more stable form than is otherwise obtainable. Thus, for example, while both monomethyl malonate and monoethyl malonate are reported in the literature as being unstable (indeed, monomethyl malonate is often sold commercially as the corresponding potassium salt), it has been surprisingly found that these compounds, when synthesized in accordance with the methodologies described herein, exhibit substantially improved stability.

The methodologies disclosed herein may be appreciated with respect to SCHEME 2 below. As seen therein, a compound A is provided which has first and second ester moieties. The compound is reacted in a liquid medium with a base having the formula $M_aX_b$, such that the first ester moiety is converted to a carboxyl moiety and the second ester moiety remains. The ratio $[X^{k-}]:[A]$ (or, as the case may be, the number of equivalents of base to A) in the liquid medium is typically no greater than 1.6 (at least in the case of linear diesters), and k>0. This reaction is followed by acidification to yield the monoester.

(SCHEME 2)

The methodology is generally applicable to compounds having first and second ester groups, and may be used to convert one of the ester groups to a carboxylic acid group. The first and second ester groups may be the same or different. Hence, $R^1$ and $R^2$ may be the same or different, and may be independently selected, for example, from the group consisting of substituted or unsubstituted alkyl, aryl or alkylaryl groups. In some embodiments, the starting ester may have more than two ester groups. However, it will be appreciated that the methodology described herein is particularly useful in creating half esters from symmetric diesters since, as noted above, conventional methods for preparing half esters typically suffer from low yields when applied to symmetric diesters, due in part to the difficulty in chemically distinguishing between the two ester groups in such materials. Such half esters include, for example, monoalkyl malonates such as monoethyl malonate, monopropyl malonate, and monobutyl malonate, as well as monoalkyl adipates.

The linking group L may be of various chain lengths and, in some embodiments, may contain one or more hetero atoms, such as, for example, N, O, or S. The linking group may also contain various functional groups, aromatic groups, or unsaturated bonds, which may be incorporated into the backbone of the linking group or which may replace one or more hydrogen atoms in an organic linking group. In some embodiments, L may be a cyclic or polycyclic moiety. In other embodiments, L may be a linear moiety.

Preferably, L is a linking group which contains 1 to 10 carbon atoms, or is a linking group having the structure —$[CH_2]_n$—, where n is an integer. In some embodiments, n may be quite large and may, for example, be greater than 100, or greater than 1000. Typically, however, n is in the range of 1 to about 50. Preferably, n is in the range of 1 to about 20, more preferably n is in the range of 1 to about 10, and most preferably, n is in the range of 1 to 5.

The base used in the methodologies disclosed herein preferably contains one or more hydroxyl groups, and more preferably is a metal hydroxide. Most preferably, the base is an alkali metal hydroxide, such as sodium hydroxide, potassium hydroxide, lithium hydroxide or cesium hydroxide. However, in some embodiments, divalent or polyvalent metal hydroxides may also be used, such as, for example, calcium hydroxide, barium hydroxide, magnesium hydroxide, strontium hydroxide, or the like. In other embodiments, non-metal hydroxides may be used, such as ammonium hydroxide or certain organic hydroxides.

The base is preferably added to the reaction solution in small portions. This may be achieved by adding the base in discrete and multiple batches, by adding the base dropwise in a continuous manner, or by slowly injecting the base into the reaction vessel with a syringe or other such device. Preferably, the reaction solution is stirred continuously during addition of the base, as through the use of a magnetic stir bar, with a solution agitator, or by other suitable means.

As noted above, the ratio $[X^{k-}]:[A]$ (or, as the case may be, the number of equivalents of base to A) in the liquid medium is typically no greater than 1.6, at least in the case of linear diesters. Typically, this ratio is within the range of about 0.5 to 1.6, preferably this ratio is within the range of about 0.7 to about 1.5, more preferably, this ratio is within the range of about 0.8 to about 1.4, even more preferably, this ratio is within the range of about 0.9 to about 1.3, and most preferably, this ratio is within the range of about 1.0 to about 1.2.

In the case of cyclic esters, or esters in which rotation about a carbon-carbon bond is prevented or is sterically hindered (especially when ester moieties are bonded to adjacent carbon atoms in such a bond), or in other cases where the half ester or partially hydrolyzed ester is relatively stable in the presence of base, larger amounts of base may be utilized in the hydrolysis reaction. In such embodiments, the ratio of the number of molar equivalents of base to the number of molar equivalents of the starting ester or diester may be larger than is the case with linear diesters. The preferred amount of base to use in such embodiments may depend on such factors as the identity of the base, the reaction rate, the relative stability of the half ester or partially hydrolyzed ester in the presence of the base, the reaction medium, the temperature of the reaction medium, and other such factors. However, in some cases, the ratio of the number of molar equivalents of base to the number of molar equivalents of the starting ester or diester may be, for example, greater than 3, greater than 5, greater than 7, or greater than about 10.

The reaction time may also vary depending on a number of factors such as, for example, the identity of the base, the reaction rate, the relative stability of the half ester or partially hydrolyzed ester in the presence of the base, the reaction medium, the temperature of the reaction medium, and other such factors, and the reaction may be quenched after the desired amount of time has passed. Typically, however, the reaction time is no greater than 90 minutes, and preferably, the reaction time is no greater than about 60 minutes. More preferably, the reaction time is within the range of about 10 minutes to about 60 minutes, and most preferably, the reaction time is within the range of about 20 minutes to about 60 minutes.

The reaction solution is preferably cooled, either during addition of the base or shortly thereafter. This may be accomplished, for example, by submerging the reaction vessel in a cooled bath, such as an ice bath. Typically, the reaction solution is cooled to a temperature below room temperature, preferably below 15° C., more preferably below 10° C., and even more preferably below 5° C. Preferably, the reaction solution is cooled to a temperature within the range of about −15° C. to about 15° C., more preferably to a temperature within the range of about −10° C. to about 10° C., and even more preferably to a temperature within the range of about −5° C. to about 5° C. Most preferably, the reaction solution is cooled to about 0° C. However, it will be appreciated that the optimal temperature in a particular case may depend on such factors as the reactants, the choice of solvent system or liquid media, the desired product, and other such factors.

The reaction solution preferably comprises mixtures of aqueous solutions of base with THF. However, it will be appreciated that other solvents, co-solvents, or liquid media may be used in place of, or in combination with, the foregoing mixtures. Thus, for example, the reaction may be implemented in a liquid medium comprising THF, $CH_3CN$, $CH_2Cl_2$, methanol, ethanol, 1-propanol, 2-propanol, DMSO, and various mixtures of the foregoing. In some embodiments, water may be the only solvent or liquid medium employed, and such embodiments may be particularly desirable in applications where green chemistry is preferred. Typically, the reaction medium will comprise at least 70% water by volume. Preferably, the reaction medium will comprise at least 80% water by volume, more preferably, the reaction medium will comprise at least 90% water by volume, and most preferably, the reaction medium will comprise at least about 93% water by volume. However, in some embodiments, the volume of water may be even higher; in such embodiments, the reaction medium may comprise at least about 97% water by volume, at least about 99% water by volume, or essentially 100% water by volume.

After reaction with the base is completed, the solution is acidified. This is preferably achieved with HCl, although various other acids may also be used for this purpose in various embodiments of the methodologies described herein. Such other acids may include, without limitation, sulfuric acid, nitric acid, and various carboxylic acids.

Although not limited to the preparation of these materials, the methodologies disclosed herein are especially useful for the preparation of monoesters of malonic acid, adipic acid, succinic acid, glutaric acid, and other linear diesters. SCHEME 3 below illustrates the synthesis of monomethyl malonate in accordance with the methodologies taught herein, and also depicts the chemical structures of other monoesters of malonic acid which may be made by analogous routes.

SCHEME 3: Synthesis of Monoesters of Malonic Acid dimethyl malonate monomethyl malonate malonic acid  monoethyl malonate  monopropyl malonate monobutyl malonate The following specific, non-limiting examples further illustrate some of the features of the methodologies disclosed herein.

COMPARATIVE EXAMPLE 1

This example illustrates the synthesis of monomethyl malonate in accordance with the methodology reported in S. Niwayama, "Highly Efficient Selective Monohydrolysis of Symmetric Diesters", *J. Org. Chem.* 2000, 65, 5834-5836.

Dimethyl malonate (1.2 mmol) was dissolved in 2 mL of THF, and 20 mL of water was added. The reaction mixture was immersed in an ice-water bath and cooled to 0° C. To this reaction mixture, 8 mL of 0.25 M NaOH was added in small portions with stirring until the consumption of the starting diester was detected by thin-layer chromatography. The reaction was stirred at the same temperature for about 30-60 minutes, and the reaction mixture was acidified with 1 M HCl at 0° C., saturated with NaCl, extracted with ethyl acetate three to four times, and dried with sodium sulfate. This extract was evaporated in vacuo and purified by silica gel column chromatography, using ethyl acetate as the eluent, to afford the half ester, monomethyl malonate, at 22% yield.

EXAMPLE 1

This example illustrates the synthesis of monomethyl malonate in accordance with the methodologies described herein, and the attendant improvement in reaction yield as compared to COMPARATIVE EXAMPLE 1.

Dimethyl malonate (159 mg, 1.20 mmol) was dissolved in 2 mL of THF, and 20 mL of water was added. The reaction mixture was cooled to 0° C. in an ice-water bath. To this mixture was added the equivalent of a 0.25 M aqueous NaOH, KOH or LiOH solution indicated in TABLE 3. In each case, the base was added dropwise with stirring. The reaction mixture was stirred for 30-60 minutes, acidified with 1M HCl at 0° C., saturated with NaCl, extracted with ethyl acetate (X4), and dried over $Na_2SO_4$. This extract was concentrated in vacuo and purified by silica gel column chromatography with hexane:ethyl acetate (3:1) and then ethyl acetate as typical eluents to afford monomethyl malonate. The yield was 119 mg (84%), a 62% improvement over the yield obtained in COMPARATIVE EXAMPLE 1.

EXAMPLES 2-9

These examples illustrate the influence of solvent systems in the synthesis of monoesters in accordance with the teachings herein, and in particular, illustrate the effect that changes in the proportion of THF have on reaction yield.

One significant difference between classical saponification and the preferred embodiment of the monohydrolysis reaction disclosed herein is the reaction media. In particular, the use in the preferred embodiment of aqueous NaOH or KOH solution in an aqueous THF media at 0° C., as opposed to the conventional use of a solid base and an alcohol medium, is found to produce a substantially cleaner reaction mixture.

In light of the foregoing, the influence of solvents in this reaction system has been studied by changing the proportion of THF. In particular, in the selective monohydrolysis of dimethyl bicyclo[2.2.1]hept-2,5-diene-2,3-dicarboxylate (SCHEME IV), the general conditions previously reported in S. Niwayama, *J. Org. Chem.* 2000, 65, were followed, with the proportion of THF as the co-solvent modified as noted in TABLE 1 below.

The results in TABLE 1 clearly indicate that decreasing the proportion of THF to below 7% does not influence the reaction rates significantly. On the other hand, increasing the proportion of THF greatly diminishes the reaction rates, and reduces the yield. Without wishing to be bound by theory, this result is believed to reflect the solubility of THF in water, with the increased proportion of THF decreasing the exposure of the carbomethoxy group to the aqueous NaOH.

TABLE 1

Effect of Volume of THF in the Monohydrolysis of a Cyclic Diester

| EXAMPLE | Volume in mL of THF (% by volume) | Time | Yield (%)$^{a,b}$ | Reaction rate constant $(L \cdot mol^{-1} \cdot s^{-1})^c$ |
|---|---|---|---|---|
| 2 | 22 (73%) | 8 h | 88 (0) | $3.26 \pm 0.02 \times 10^{-3}$ |
| 3 | 18 (60%) | 6 h 30 min | 81 (1.2) | $6.06 \pm 0.12 \times 10^{-3}$ |
| 4 | 14 (47%) | 5 h 20 min | 84 (0.4) | $1.10 \pm 0.02 \times 10^{-2}$ |
| 5 | 10 (33%) | 3 h | 90 (1.6) | $2.06 \pm 0.23 \times 10^{-2}$ |
| 6 | 6 (20%) | 70 min | 94 (1.2) | $2.56 \pm 0.06 \times 10^{-2}$ |
| 7 | $2^d$ (7%) | 70 min | >99 (0) | $4.70 \pm 0.02 \times 10^{-2}$ |
| 8 | 1 (3%) | 70 min | >99 (0) | $4.81 \pm 0.10 \times 10^{-2}$ |
| 9 | 0 (0%) | 70 min | >99 (0) | $4.59 \pm 0.07 \times 10^{-2}$ |

$^a$Isolated yield of half ester. Recovered diester is shown in parenthesis.
$^b$Obtained by procedure B in the experimental section.
$^c$Obtained by procedure C in the experimental section.
$^d$The same conditions reported in S. Niwayama, *J. Org. Chem.* 2000, 65, 5834.

(SCHEME 4)

EXAMPLES 10-16

These examples illustrate the influence of solvent systems on the synthesis of monoesters in accordance with the teachings herein, and in particular, illustrate the effect that changes in co-solvents have on yield and reaction rate.

A variety of co-solvents were employed in the selective monohydrolysis of dimethyl bicyclo[2.2.1]hept-2,5-diene-2,3-dicarboxylate (SCHEME V), using the same general conditions of 7% co-solvent and reaction temperature as in EXAMPLE 7 above. The results are summarized in TABLE 2 below.

From these results, it is apparent that methylene chloride, which has little miscibility with water, decreases the reaction rate significantly, a result again believed to be due to the reduced exposure of the carboalkoxy group to the aqueous NaOH. This result is similar to the cases in which large percentages of THF are applied as shown in TABLE 1. On the other hand, other co-solvents investigated that are water-miscible to a small or great extent do not appear to change the reaction rate significantly. The isolated yields of half ester appear to be the highest when THF, acetonitrile, or no co-solvent is used, and slightly decrease when an alcohol is used as a co-solvent. These results indicate that the decreased yields may be due to the formation of the small amount of the corresponding diacid, and/or to the difficulty of extracting the product. Overall, THF and acetonitrile appear to be the best co-solvents among the solvents tested in this study for this selective monohydrolysis reaction.

Without wishing to be bound by theory, the foregoing results, coupled with the results of EXAMPLES 2-9, appear to suggest that (a) in the reaction mixture, the small amount of THF or acetonitrile is dissolved in the larger amount of water, making one aqueous phase; (b) that the diester participates in the reaction as the second phase; and (c) that the monohydrolysis occurs at the interface between the aqueous phase and the diester. The major role of THF or acetonitrile as a co-solvent is likely that of dispersing the starting diesters more smoothly throughout the reaction medium. This role is particularly advantageous when the starting diester is a solid.

This solvent effect has also been applied to selective monohydrolysis of diesters of molanic acid derivatives. There, it was found that the use of acetonitrile, instead of THF, improved the yields of the half esters to some extent.

Recently, water-mediated reactions have become important as environmentally friendly reactions in green chemistry. The reaction described here is believed to be among the first examples of water-mediated reactions being applied to desymmetrization.

TABLE 2

Effects of Co-solvents in the Monohydrolysis of Dimethyl Malonate

| EXAMPLE | Co-Solvent | Yield (%)$^{a,b}$ | Reaction rate constant $(L \cdot mol^{-1} \cdot s^{-1})^c$ |
|---|---|---|---|
| 10 | THF$^d$ | >99 (0) | $4.70 \pm 0.02 \times 10^{-2}$ |
| 11 | $CH_3CN$ | >99 (0) | $4.85 \pm 0.40 \times 10^{-2}$ |
| 12 | methanol | 90 (0.8) | $3.73 \pm 0.50 \times 10^{-2}$ |
| 13 | ethanol | 86 (0) | $3.48 \pm 0.06 \times 10^{-2}$ |
| 14 | 2-propanol | 88 (0.8) | $3.29 \pm 0.02 \times 10^{-2}$ |
| 15 | $CH_2Cl_2$ | 9 (89) | $8.60 \pm 0.27 \times 10^{-4}$ |
| 16 | None | >99 (0) | $4.59 \pm 0.07 \times 10^{-2}$ |

$^a$Isolated yield of half ester. Recovered diester is shown in parenthesis.
$^b$Obtained by procedure B in the experimental section.
$^c$Obtained by procedure C in the experimental section.
$^d$The same conditions reported in S. Niwayama, *J. Org. Chem.* 2000, 65, 5834.

(SCHEME 5)

EXAMPLE 17-25

These examples illustrate the effect on yield of different bases at different equivalents in monohydrolysis reactions of the type described herein.

When selective monohydrolysis of dimethylmalonate was conducted according to the conditions reported in S. Niwayama, *J. Org. Chem.* 2000, 65, 5834-5836, only 22% of the corresponding half ester was obtained. Without wishing to be bound by theory, this result is thought to be possibly due to decarboxylation and overuse of the base, as well as lack of the ideal conformation of the starting diester. Consequently, the effect on reaction yield of various alkali metal hydroxides in varying amounts (1.2, 1.0, or 0.8 equivalent) was explored in the monohydrolysis of dimethyl malonate. The procedures are the same as those we reported before. Id. TABLE 3 is a summary of the type of base, the equivalent, and the reaction times.

TABLE 3

Effect Of Base On Yield

| Example | Base | Equivalent | Time (hr) | Half Ester (%)[a] |
|---|---|---|---|---|
| 17 | LiOH | 0.8 | 1 | 61 (13) |
| 18 | NaOH | 0.8 | 0.5 | 62 (3) |
| 19 | KOH | 0.8 | 1 | 84 |
| 20 | LiOH | 1.0 | 1 | 80 (10) |
| 21 | NaOH | 1.0 | 1 | 82 (10) |
| 22 | KOH | 1.0 | 1 | 83 (3) |
| 23 | LiOH | 1.2 | 1 | 75 (10) |
| 24 | NaOH | 1.2 | 1 | 83 (5) |
| 25 | KOH | 1.2 | 1 | 74 |

[a]Isolated yield of the half ester. The amount of recovered diester is indicated in parenthesis (%).

(SCHEME 6)

As these results indicate, the reactivity slightly increased with the use of KOH over NaOH with comparable selectivity, while LiOH slightly decreased the selectivity and reactivity. In these reactions, the isolated yields of the half ester and diester indicated that, although a small amount of diacid (malonic acid) possibly formed, it was not extracted during the work-up procedures. This result, may have been due to the small hydrophobic portion of this compound, demonstrates one of the advantages of this reaction. The product in this monohydrolysis reaction, monomethyl malonate (see EXAMPLE 54), is among those most frequently applied to organic synthesis. This route appears to allow the highly practical synthesis of monomethyl malonate with a reaction time of only about one hour, which illustrates the synthetic utility of this monohydrolysis.

EXAMPLES 26-37

These examples illustrate the effect of co-solvent and the type and number of equivalents of base on the monohydrolysis of dimethyl malonate on a more highly concentrated scale.

EXAMPLE 37 was prepared by the following procedure (SCHEME 7). In a 1 L-sized one-necked flask, equipped with a magnetic stirrer, was placed 158.33 g (1.2 mol) of dimethyl malonate, and 10 mL of acetonitrile was added to dissolve the dimethyl malonate. After the solution was stirred for one minute, the reaction mixture was cooled to 0° C. with an ice-water bath. To this mixture, 100 mL of water was added and stirred for 30 minutes. To this reaction mixture was added 240 mL of 5M aqueous KOH solution (1.2 mol) dropwise with stirring for a period of 15 minutes using an additional funnel (the 5M KOH solution was titrated with 20 mL of 0.5 M oxalic acid, which was purchased from the Mallinckrodt Company, Hazelwood, Mo.). When the addition was completed, the reaction mixture was stirred for an additional 60 minutes, during which it was covered with a stopper and held in the ice-water bath.

The reaction mixture was acidified with 150 mL of 12 M aqueous HCl solution in the ice-water bath, saturated with NaCl, and extracted with five 500 mL portions of ethyl acetate with a 1 L separatory funnel. The extract was washed with 500 mL of a saturated aqueous NaCl solution. The ethyl acetate extract was dried over approximately 100 g of anhydrous sodium sulfate. After the drying agent was removed by gravity filtration, the ethyl acetate solution was concentrated by a rotary evaporator, and distilled under a reduced pressure at 2.5 mmHg. The fraction showing a boiling point of 91-92° C. was collected to yield monomethyl malonate as a colorless oil. The yield was 114.77 g (81%) was recovered at 45° C. and 4% of dimethyl malonate and 1% of malonic acid were found.

EXAMPLES 26-36 were prepared using the general procedure of EXAMPLE 37 and using the modified reaction conditions noted in TABLE 4 below.

TABLE 4

Hydrolysis of Dimethyl Malonate At More Concentrated Scale

| EXAMPLE | Base | Eq. | Co-solvent | Time | Half ester (%) | Recovered Diester (%) |
|---|---|---|---|---|---|---|
| 26 | NaOH | 0.8 | THF | 1 h | 67.1 | 24.5 |
| 27 | NaOH | 1.0 | THF | 1 h | 81.9 | 7.0 |
| 28 | NaOH | 1.2 | THF | 1 h | 67.4 | 1.7 |
| 29 | NaOH | 0.8 | CH$_3$CN | 1 h | 69.0 | 23.9 |
| 30 | NaOH | 1.0 | CH$_3$CN | 1 h | 82.1 | 6.6 |
| 31 | NaOH | 1.2 | CH$_3$CN | 1 h | 71.3 | 0 |
| 32 | KOH | 0.8 | THF | 1 h | 75.0 | 20.9 |
| 33 | KOH | 1.0 | THF | 1 h | 83.1 | 3.4 |
| 34 | KOH | 1.2 | THF | 1 h | 72.4 | 0 |
| 35 | KOH | 0.8 | CH$_3$CN | 1 h | 75.7 | 16.3 |
| 36 | KOH | 1.0 | CH$_3$CN | 1 h | 84.5 | 0 |
| 37 | KOH | 1.2 | CH$_3$CN | 1 h | 69.1 | 0 |

(SCHEME 7)

EXAMPLES 38-53

These examples illustrate the application of the methodologies described herein to a wide range of dialkyl malonates and their derivatives using aqueous NaOH or KOH as a base.

EXAMPLE 1 was repeated using the various diesters depicted in TABLE 5. The results are summarized in TABLE 5. Most of these diesters are commercially available. Some diesters were prepared by the standard Fischer esterification.

Unlike classical monosaponification, which tends to yield a complex yellowish reaction mixture, in all cases in these reactions, only pure half esters, starting diesters, and (in rare cases) diacids, if extant, were isolated. In some cases, based on the percentage of the yield of the half ester and recovered diester, a small amount of the diacid appeared to have formed. However, these diacids were not extracted when the reaction mixture was worked up. All the obtained half esters had excellent purity, giving sharp elemental analysis data. No decarboxylated products were detected in any of the monohydrolysis reactions.

Overall, KOH tends to be more reactive and slightly more selective than NaOH, as was observed in the results depicted in TABLE 5. This tendency may be best illustrated in the monohydrolysis of diethyl phenymalonate (EXAMPLES 50-51), which showed enhanced reactivity and selectivity with the use of KOH, compared to the results previously obtained with the use of NaOH for monohydrolysis of the same diester (see Id.).

The results in TABLE 5 suggest that selectivity may increase with the hydrophobicity of the molecule. For example, the yields of the half ester increase with ester groups that are more hydrophobic in comparison to the monohydrolysis of diesters (see TABLE 5, EXAMPLES 50-53). The yields of half esters become even higher when the additional methyl or phenyl group is introduced (EXAMPLES 42-53). Without wishing to be bound by theory, it is believed that, in this monohydrolysis reaction, upon the monohydrolysis of the two identical ester groups, inter- and/or intramolecular hydrophobic attractive interactions within the remaining portion of the molecule may play an important role for this high selectivity, as such aggregates may be protected from further hydrolysis. Therefore, this trend may explain such potential hydrophobic interaction.

The only noted exception to the foregoing observation is in the monohydrolysis of dipropyl phenylmalonate (EXAMPLES 52 and 53). This result may be due to the extended period of the reaction time, which also sometimes allowed isolation of a visible amount of the corresponding diacid. Here, the use of acetonitrile (another slightly polar aprotic solvent that is slightly miscible with water) instead of THF as a co-solvent helped accelerate the reaction time to some extent, increasing the yield of the half ester by about 10%. Previously, the influence of the co-solvent in this monohydrolysis was studied and it was found that a slightly polar aprotic solvent with a small degree of miscibility with water appears to be an effective co-solvent. It may also be possible that the introduction of several bulky groups prohibited adoption of a preferable conformation for this selectivity.

TABLE 5

Hydrolysis of Diesters

| EXAMPLE | Diester | Base | Equivalents | Time (hr) | Half ester (%)[a] |
|---|---|---|---|---|---|
| 38 | EtO-C(O)-CH2-C(O)-OEt | KOH | 0.8 | 1 | 90 |
| 39 | EtO-C(O)-CH2-C(O)-OEt | NaOH | 1.0 | 1 | 86 (3) |
| 40 | PrO-C(O)-CH2-C(O)-OPr | KOH | 0.8 | 1 | 91 (8) |
| 41 | PrO-C(O)-CH2-C(O)-OPr | NaOH | 1.0 | 0.5 | 92 (8) |
| 42 | MeO-C(O)-CH(CH3)-C(O)-OMe | KOH | 1.2 | 1.5 | 94 (2) |
| 43 | MeO-C(O)-CH(CH3)-C(O)-OMe | NaOH | 1.2 | 1.5 | 93 (6) |

TABLE 5-continued

Hydrolysis of Diesters

| EXAMPLE | Diester | Base | Equivalents | Time (hr) | Half ester (%)[a] |
|---|---|---|---|---|---|
| 44 | EtO-C(O)-CH(CH₃)-C(O)-OEt | KOH | 1.2 | 1.5 | 96 (2) |
| 45 | EtO-C(O)-CH(CH₃)-C(O)-OEt | NaOH | 1.2 | 1.5 | 96 (4) |
| 46 | PrO-C(O)-CH(CH₃)-C(O)-OPr | KOH | 1.2 | 1.75 | 97 (3) |
| 47 | PrO-C(O)-CH(CH₃)-C(O)-OPr | NaOH | 1.2 | 1.75 | 98 (2) |
| 48 | MeO-C(O)-CH(Ph)-C(O)-OMe | KOH | 1.2 | 1 | 95 (5) |
| 49 | MeO-C(O)-CH(Ph)-C(O)-OMe | NaOH | 1.2 | 1 | 95 (5) |
| 50 | EtO-C(O)-CH(Ph)-C(O)-OEt | KOH | 1.2 | 5 | 94 (4) |
| 51 | EtO-C(O)-CH(Ph)-C(O)-OEt | NaOH | 1.2 | 5 | 86 (13) |
| 52 | PrO-C(O)-CH(Ph)-C(O)-OPr | KOH | 0.8 | 33 | 77 (22) |
| 53 | PrO-C(O)-CH(Ph)-C(O)-OPr | NaOH | 0.8 | 33 | 68 (32) |

[a] Isolated yield of the half ester. The amount of recovered diester is indicated in parenthesis (%).
[b] Acetonitrile was used instead of THF as co-solvent.

In summary, highly practical conditions have been found with aqueous KOH or NaOH with THF or acetonitrile as a co-solvent at 0° C. to selectively monohydrolyze a series of dialkyl malonates and their derivatives. The yields here are the highest among the yields reported previously (Id.). All the half esters prepared showed excellent purity and were stable over a long period of time. It was also found that the selectivity generally increases as the hydrophobicity of the ester group increases. Such tendencies suggest that hydrophobic attractive interaction may play an important role in this selectivity.

EXAMPLE 54

This example illustrates the synthesis of monomethyl malonate.

In a 100 mL-sized one-necked flask, equipped with a magnetic stirrer, was placed 15.833 g (0.12 mol) of dimethyl malonate (purchased from ACROSS chemicals), and 1 mL of THF was added to dissolve this dimethyl malonate. After the solution was stirred for one minute, the reaction mixture was cooled to 0° C. with an ice-water bath. To this mixture, 10 mL of water was added and stirred for 30 minutes. To this reaction mixture was added 26.4 mL (1.1 equivalents) of 5M aqueous NaOH solution (97% minimum assay obtained from EMD Chemicals Inc., Gibbstown, N.J.). This solution was added dropwise with stirring over a period of 5 minutes. When the addition was completed, the reaction mixture was stirred for an additional 30 minutes, during which it was covered with a stopper and kept in the ice-water bath.

The reaction mixture was acidified with 30 mL of 6 M aqueous HCl solution in the ice-water bath, saturated with NaCl, and extracted with five 50 mL portions of ethyl acetate with a 250 mL separatory funnel. The extract was washed with 50 mL of a saturated aqueous NaCl solution. The ethyl acetate extract was dried over approximately 10 g of anhydrous sodium sulfate. After the drying agent was removed by gravity filtration, the ethyl acetate solution was concentrated by a rotary evaporator, and distilled under a reduced pressure at 2.5 mmHg. The fraction showing a boiling point of 91-92° C. was collected to yield monomethyl malonate as a colorless oil. The yield was 82%.

Monomethyl malonate. Oil. $^1$H NMR (300 MHz, CDCl$_3$) δ=3.47 (2H, s), 3.79 (3H, s), 11.4 (1H, br.s); $^{13}$C NMR (75 MHz, CDCl$_3$) δ=40.50, 52.50, 167.03, 171.46; IR (neat, cm$^{-1}$) 1741, 1746, 2960-3185; Anal. Calcd for C$_4$H$_6$O$_4$: C, 40.68; H, 5.12. Found: C, 40.51; H, 5.34.

EXAMPLE 55

This example illustrates the synthesis of monoethyl malonate.

Diethyl malonate (192 mg, 1.2 mmol) was dissolved in 2 mL of THF, and 20 mL of water was added. The reaction mixture was cooled to 0° C. in an ice-water bath. To this mixture was added the indicated equivalent of a 0.25 M aqueous NaOH, or KOH solution dropwise with stirring. The reaction mixture was stirred for one hour, and acidified with 1M HCl at 0° C., saturated with NaCl, extracted with ethyl acetate (X4), and dried over Na$_2$SO$_4$. This extract was concentrated in vacuo and purified by silica gel column chromatography, first with hexane:ethyl acetate (3:1) and then with ethyl acetate, to afford monoethyl malonate.

Monoethyl malonate. Oil. $^1$H NMR (300 MHz, CDCl$_3$) δ=1.31 (3H, t, J=7.2), 3.44 (2H, s), 4.25 (2H, q, J=7.2), 10.62 (1H, br.s); $^{13}$C NMR (75 MHz, CDCl$_3$) δ=13.90, 40.78, 61.90, 166.87, 171.48; IR (neat, cm$^{-1}$) 1736, 1741, 2914-3182; Anal. Calcd for C$_5$H$_8$O$_4$: C, 45.46; H, 6.10. Found: C, 45.83; H, 6.30.

EXAMPLE 56

This example illustrates the synthesis of monopropyl malonate.

Dipropyl malonate (226 mg, 1.2 mmol) was dissolved in 2 mL of THF, and 20 mL of water was added. The reaction mixture was cooled to 0° C. in an ice-water bath. To this mixture was added the indicated equivalent of a 0.25 M aqueous NaOH, or KOH solution dropwise with stirring. The reaction mixture was stirred for 30 minutes to one hour, and acidified with 1M HCl at 0° C., saturated with NaCl, extracted with ethyl acetate (X4), and dried over Na$_2$SO$_4$. This extract was concentrated in vacuo and purified by silica gel column chromatography, first with hexane:ethyl acetate (3:1) and then with ethyl acetate, to afford monopropyl malonate.

Oil. $^1$H NMR (300 MHz, CDCl$_3$) δ=0.96 (3H, t, J=7.7), 1.70 (2H, m), 3.46 (2H, s), 4.15 (2H, q, J=7.2), 10.18 (1H, br.s); $^{13}$C NMR (75 MHz, CDCl$_3$) δ=10.12, 21.69, 40.89, 67.42, 166.81, 171.74; IR (neat, cm$^{-1}$) 1723, 1740, 2883-3181; Anal. Calcd for C$_6$H$_{10}$O$_4$: C, 49.31; H, 6.90. Found: C, 49.43; H, 7.14.

EXAMPLE 57

This example illustrates the synthesis of monomethyl methylmalonate.

Dimethyl methylmalonate (175 mg, 1.2 mmol) was dissolved in 2 mL of THF, and 20 mL of water was added. The reaction mixture was cooled to 0° C. in an ice-water bath. To this mixture was added the 1.2 equivalents of a 0.25 M aqueous NaOH, or KOH solution dropwise with stirring. The reaction mixture was stirred for 1.5 hours, and acidified with 1M HCl at 0° C., saturated with NaCl, extracted with ethyl acetate (X4), and dried over Na$_2$SO$_4$. This extract was concentrated in vacuo and purified by silica gel column chromatography, first with hexane:ethyl acetate (3:1) and then with ethyl acetate, to afford monomethyl methylmalonate.

Oil. $^1$H NMR (300 MHz, CDCl$_3$) δ=1.43 (3H, d, J=7.2), 3.47 (1H, q, J=7.2), 3.73 (3H, s), 9.42 (1H, br.s); $^{13}$C NMR (75 MHz, CDCl$_3$) δ=13.08, 45.45, 52.39, 170.16, 175.38; IR (neat, cm$^{-1}$) 1721, 1739, 2956-3202; Anal. Calcd for C$_5$H$_8$O$_4$: C, 45.46; H, 6.10. Found: C, 45.65; H, 5.94.

EXAMPLE 58

This example illustrates the synthesis of monoethyl methylmalonate.

Diethyl methylmalonate (209 mg, 1.2 mmol) was dissolved in 2 mL of THF, and 20 mL of water was added. The reaction mixture was cooled to 0° C. in an ice-water bath. To this mixture was added the 1.2 equivalents of a 0.25 M aqueous NaOH, or KOH solution dropwise with stirring. The reaction mixture was stirred for 1.5 hours, and acidified with 1M HCl at 0° C., saturated with NaCl, extracted with ethyl acetate (X4), and dried over Na$_2$SO$_4$. This extract was concentrated in vacuo and purified by silica gel column chromatography, first with hexane:ethyl acetate (3:1) and then with ethyl acetate, to afford monoethyl methylmalonate.

Oil. $^1$H NMR (300 MHz, CDCl$_3$) δ=1.24 (3H, t, J=7.2), 1.40 (3H, d, J=7.5), 3.44 (1H, q, J=7.2), 4.18 (2H, q, J=7.2), 11.21 (1H, br, s); $^{13}$C NMR (75 MHz, CDCl$_3$) δ=13.44, 13.90, 45.93, 61.70, 169.83, 176.00; IR (neat, cm$^{-1}$) 1722, 1735, 2946-3200; Anal. Calcd for $C_6H_{10}O_4$: C, 49.31; H, 6.90. Found: C, 49.68; H, 6.75.

EXAMPLE 59

This example illustrates the synthesis of monopropyl methylmalonate.

Dipropyl methylmalonate, 7, (243 mg, 1.2 mmol) was dissolved in 2 mL of THF, and 20 mL of water was added. The reaction mixture was cooled to 0° C. in an ice-water bath. To this mixture was added the 1.2 equivalents of a 0.25 M aqueous NaOH, or KOH solution dropwise with stirring. The reaction mixture was stirred for one hour and 45 minutes, and acidified with 1M HCl at 0° C., saturated with NaCl, extracted with ethyl acetate (X4), and dried over $Na_2SO_4$. This extract was concentrated in vacuo and purified by silica gel column chromatography, first with hexane:ethyl acetate (3:1) and then with ethyl acetate, to afford monopropyl methylmalonate.

Oil. $^1H$ NMR (300 MHz, $CDCl_3$) δ=0.90 (3H, t, J=7.5), 1.42 (3H, d, J=7.2), 1.64 (2H, m), 3.46 (1H, q, J=7.2), 4.09 (2H, q, J=7.2), 10.62 (1H, br, s); $^{13}C$ NMR (75 MHz, $CDCl_3$) δ=10.17, 13.51, 21.77, 45.94, 67.24, 169.93, 175.96; IR (neat, $cm^{-1}$) 1717, 1739, 2883-2971; Anal. Calcd for $C_7H_{12}O_4$: C, 52.49; H, 7.55. Found: C, 52.74; H, 7.49.

EXAMPLE 60

This example illustrates the synthesis of monomethyl phenylmalonate.

Dimethyl phenylmalonate (250 mg, 1.2 mmol) was dissolved in 2 mL of THF, and 20 mL of water was added. The reaction mixture was cooled to 0° C. in an ice-water bath. To this mixture was added the 1.2 equivalents of a 0.25 M aqueous NaOH, or KOH solution dropwise with stirring. The reaction mixture was stirred for one hour, and acidified with 1M HCl at 0° C., saturated with NaCl, extracted with ethyl acetate (X4), and dried over $Na_2SO_4$. This extract was concentrated in vacuo and purified by silica gel column chromatography, first with hexane:ethyl acetate (3:1) and then with ethyl acetate, to afford monomethyl phenylmalonate.

White solid; m.p. 92-93° C.; $^1H$ NMR (300 MHz, $CDCl_3$) δ=3.75 (3H, s), 4.65 (2H, s), 7.4 (5H, m), 9.0 (1H, br.s); $^{13}C$ NMR (75 MHz, $CDCl_3$) δ=53.06, 57.33, 128.55, 128.77, 129.15, 131.96, 168.59, 173.25; IR (neat, $cm^{-1}$) 1717, 1740, 2956-3212; Anal. Calcd for $C_{10}H_{10}O_4$: C, 61.85; H, 5.19. Found: C, 61.92; H, 5.40.

EXAMPLE 61

This example illustrates the synthesis of monoethyl phenylmalonate.

Dimethyl phenylmalonate (284 mg, 1.2 mmol) was dissolved in 2 mL of THF, and 20 mL of water was added. The reaction mixture was cooled to 0° C. in an ice-water bath. To this mixture was added the 1.2 equivalents of a 0.25 M aqueous NaOH, or KOH solution dropwise with stirring. The reaction mixture was stirred for five hours, and acidified with 1M HCl at 0° C., saturated with NaCl, extracted with ethyl acetate (X4), and dried over $Na_2SO_4$. This extract was concentrated in vacuo and purified by silica gel column chromatography, first with hexane:ethyl acetate (3:1) and then with ethyl acetate, to afford monoethyl phenylmalonate.

White solid; m.p. 74° C. (lit 76-77° C.)$^{3a}$; $^1H$ NMR (300 MHz, $CDCl_3$) δ=1.25 (3H, t, J=7.2), 4.24 (2H, q, J=7.2), 4.64 (1H, s), 7.4 (5H, m), 9.78 (1H, br, s); $^{13}C$ NMR (75 MHz, $CDCl_3$) δ=13.81, 57.51, 62.10, 128.39, 128.62, 129.13, 132.01, 167.95, 173.84; IR (neat, $cm^{-1}$) 1717, 1737, 2941-3190; Anal. Calcd for $C_{11}H_{12}O_4$: C, 63.45; H, 5.81. Found: C, 63.30; H, 5.80.

EXAMPLE 62

This example illustrates the synthesis of monopropyl phenylmalonate.

Dipropyl phenylmalonate (317 mg, 1.2 mmol) was dissolved in 2 mL of acetonitrile, and 20 mL of water was added. The reaction mixture was cooled to 0° C. in an ice-water bath in a cold room. To this mixture was added the 0.8 equivalents of a 0.25 M aqueous NaOH, or KOH solution dropwise with stirring. The reaction mixture was stirred for 33 hours in a cold room maintained at around 4° C., and acidified with 1M HCl at 0° C., saturated with NaCl, extracted with ethyl acetate (X4), and dried over $Na_2SO_4$. This extract was concentrated in vacuo and purified by silica gel column chromatography, first with hexane:ethyl acetate (3:1) and then with ethyl acetate, to afford monopropyl phenylmalonate.

Oil. $^1H$ NMR (300 MHz, $CDCl_3$) δ=0.87 (3H, t, J=7.5), 1.64 (2H, m, J=7.2), 4.11 (2H, m), 4.64 (1H, s), 7.4 (5H, m), 8.02 (1H, br, s); $^{13}C$ NMR (75 MHz, $CDCl_3$) δ=10.15, 21.74, 57.47, 67.72, 128.48, 128.74, 129.12, 132.21, 168.41, 173.07; IR (neat, $cm^{-1}$) 1717, 1736, 2881-3067; Anal. Calcd for $C_{12}H_{14}O_4$: C, 64.85; H, 6.35. Found: C, 65.17; H, 6.61.

EXAMPLES 63-65

These examples illustrate the effect that the hydrophobicity of the ester groups can have on reaction time.

Using the general reaction conditions indicated below, a series of half esters having increasingly hydrophobic alkyl groups were prepared (SCHEME 8), and the reaction times for the analogs were noted. The results are set forth in TABLE 6 below.

TABLE 6

| Effect of the Hydrophobicity of the Carboxyl Groups | | | | |
|---|---|---|---|---|
| EXAMPLE | R | Yield (%) | Reaction Time (min) | Rate Constant (L · $mol^{-1}$ · $s^{-1}$) |
| 63 | —$CH_3$ | >99 | 70 | $2.70 \times 10^{-2}$ |
| 64 | —$CH_2CH_3$ | 98 | 210 | $1.10 \times 10^{-2}$ |
| 65 | —$CH(CH_3)_2$ | 96 | 1140 | |

(SCHEME 8)

As these results indicate, increasing the hydrophobicity of the alkyl group R produced a corresponding increase in reaction time. In the case of cyclic diesters of the type utilized in this reaction, it was found that reaction times could be reduced through the use of additional base, without a significant decrease in product yield (see EXAMPLE 82 below). By contrast, the use of additional base was observed to give rise to reduced product yield in the case of the hydrolysis of linear diesters such as, for example, dialkyl malonates and dialkyl adipates.

EXAMPLES 66-81

These examples illustrate the effect that reaction time and choice of base has on the ratio of half ester to diacid.

Various bases were utilized in the hydrolysis reaction depicted in SCHEME 9 below. The ratio of half ester to diacid was determined by $^1$H NMR spectroscopy, and is set forth in TABLES 7-10 below.

(SCHEME 9)

TABLE 7

Reaction Time Using LiOH As Base

| EXAMPLE | Reaction Time (min.) | a (%) | b (%) | a:b |
|---|---|---|---|---|
| 66 | 20 | 66.2 | 33.8 | 1.96 |
| 67 | 25 | 61.1 | 38.9 | 1.57 |
| 68 | 30 | 59.2 | 40.8 | 1.45 |
| 69 | 35 | 55.9 | 44.1 | 1.27 |

TABLE 8

Reaction Time Using NaOH As Base

| EXAMPLE | Reaction Time (min.) | a (%) | b (%) | a:b |
|---|---|---|---|---|
| 70 | 20 | 67.8 | 32.2 | 2.11 |
| 71 | 25 | 67.4 | 32.6 | 2.07 |
| 72 | 30 | 61.4 | 38.6 | 1.59 |
| 73 | 35 | 60.9 | 39.1 | 1.56 |

TABLE 9

Reaction Time Using KOH As Base

| EXAMPLE | Reaction Time (min.) | a (%) | b (%) | a:b |
|---|---|---|---|---|
| 74 | 10 | 86.8 | 13.2 | 6.58 |
| 75 | 15 | 74.5 | 25.5 | 2.92 |
| 76 | 20 | 69.0 | 31.0 | 2.23 |
| 77 | 25 | 67.9 | 32.1 | 2.12 |

TABLE 10

Reaction Time Using CsOH As Base

| EXAMPLE | Reaction Time (min.) | a (%) | b (%) | a:b |
|---|---|---|---|---|
| 78 | 10 | 82.2 | 17.8 | 4.62 |
| 79 | 15 | 67.8 | 32.2 | 2.11 |
| 80 | 20 | 64.6 | 35.4 | 1.82 |
| 81 | 25 | 51.9 | 48.1 | 1.08 |

As these results indicate, in the case of the particular linear diester being studied, as reaction time increases beyond a certain point, the amount of half ester decreases, and the amount of diacid increases. This result was observed for all four bases.

EXAMPLE 82

This example illustrates the time dependence of the monohydrolysis of cyclic diesters.

Dimethyl bicyclo[2.2.1]hept-2,5-diene-2,3-dicarboxylate (1.2 mmol) was dissolved in 2 mL of THF, and 20 mL of water was added. The reaction mixture was immersed in an ice-water bath and cooled to 0° C. To this reaction mixture, 8 mL of 0.25 M NaOH was added in small portions with stirring. The mixture was periodically quenched, and the products were monitored by $^1$H NMR. From the integral curves corresponding to certain peaks assigned to the diester, the half-ester and the diacid, the molar ratios of diester, half-ester and diacid were determined. The results are plotted in FIG. 1.

Figure 1:
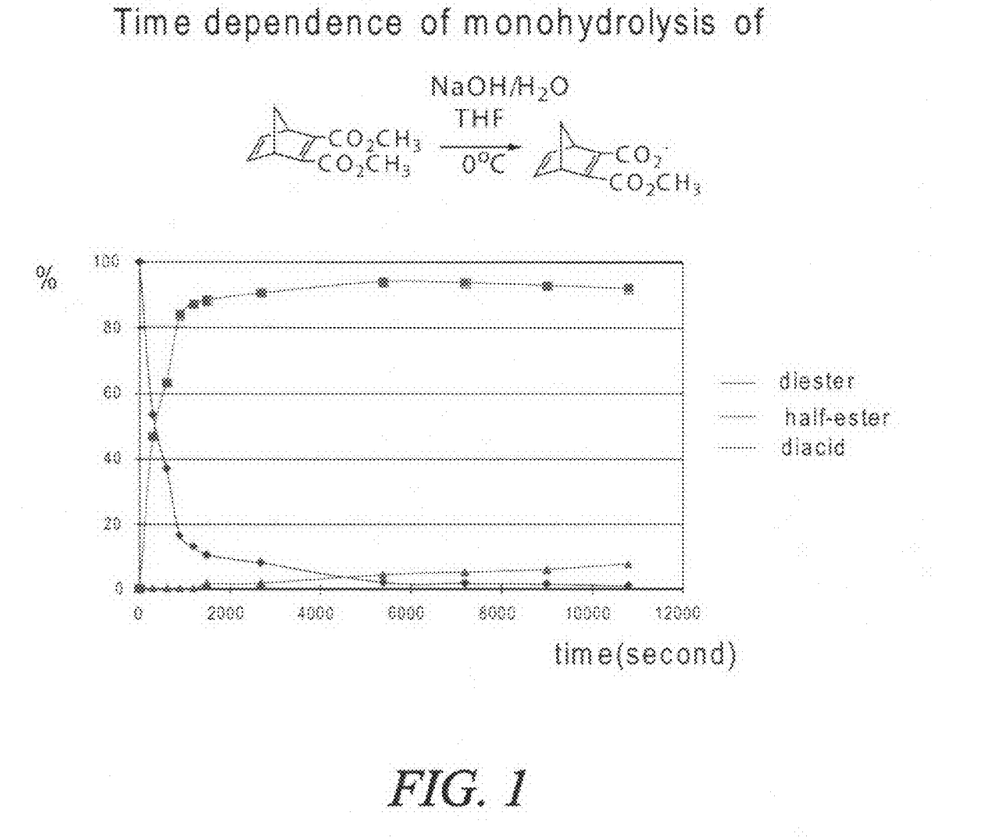
FIG. 1 is a graph of the time dependence of the monohydrolysis of a diester.

As seen therein, in the case of the hydrolysis of dimethyl bicyclo[2.2.1]hept-2,5-diene-2,3-dicarboxylate, after the reaction was essentially complete (as indicated by the remaining amount of diester), the amount of half ester decreased only slightly over time, and the amount of diacid increased only slightly over time. Similar results were observed with other cyclic diesters. These results suggest that half esters of this type are relatively stable to base.

EXAMPLES 83-86

These examples illustrate the time dependence of the monohydrolysis of linear diesters.

Figure 2:
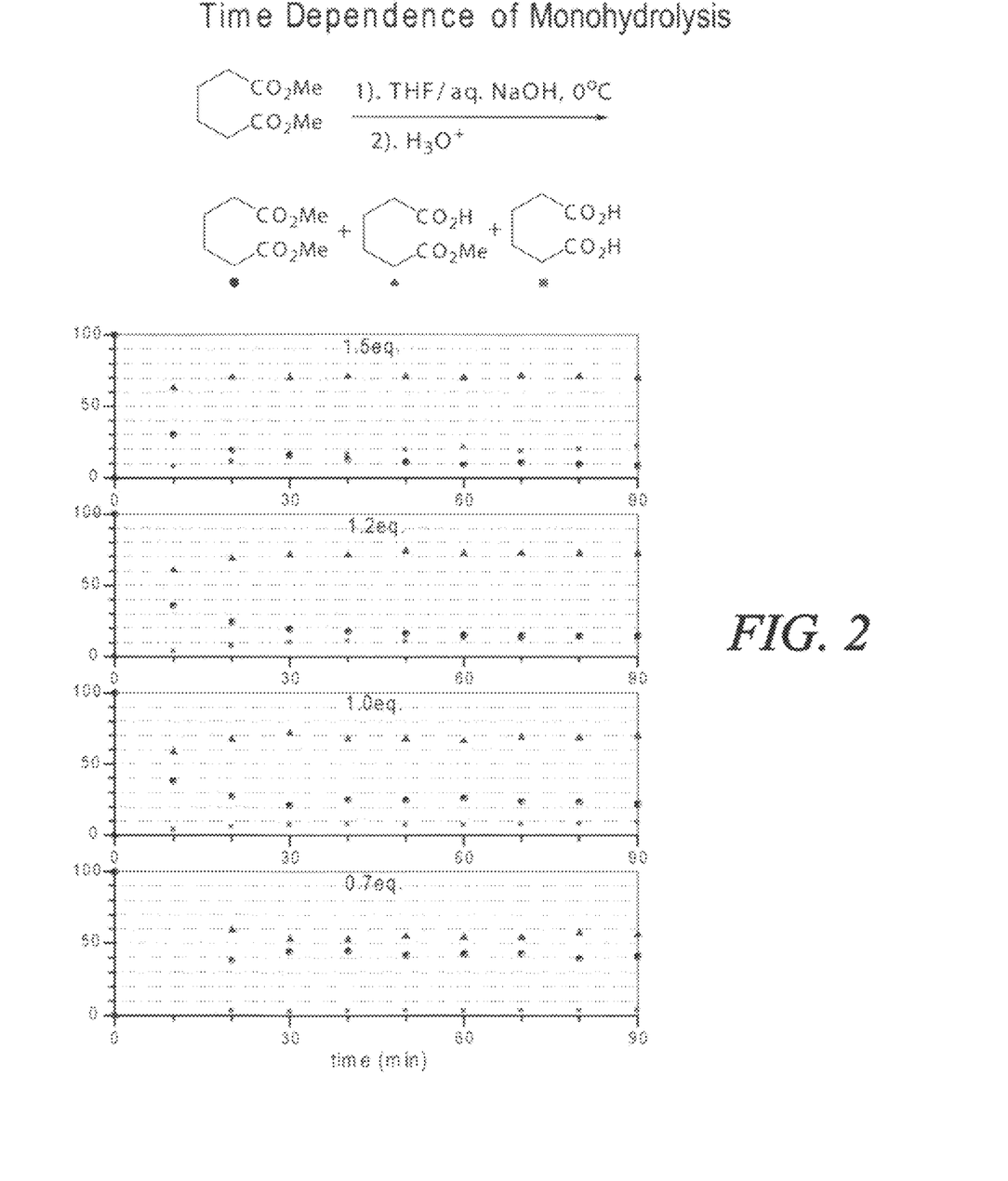
FIG. 2 is a graph of the time dependence of the monohydrolysis of a diester.

EXAMPLE 82 was repeated, except that dimethyl adipate was substituted for dimethyl bicyclo[2.2.1]hept-2,5-diene-2, 3-dicarboxylate, and four different equivalents of base (0.7, 1.0, 1.2 and 1.5) were utilized. The peaks corresponding to the diester, half-ester, and diacid were monitored by HPLC, and the corresponding ratios were plotted as shown in FIG. 2.

As seen therein, as the amount of base increased, the yield of diacid also increased. Similar results were observed in the monohydrolysis of other linear diesters. These results suggest that half esters of this type are less stable to base than cyclic diesters of the type investigated in EXAMPLE 82. Hence, while the reaction rate of such cyclic diesters may be increased through the addition of more base without producing a significant adverse effect in product yield, such is not the case for linear diesters.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A method for hydrolyzing an ester, comprising:
providing a first symmetric compound A having first and second ester moieties; and
reacting the compound with a base having the formula $M_aX_b$, followed by acidification, to form a second compound B in which the first ester moiety is converted to a carboxyl moiety and the second ester moiety remains;
wherein A is reacted with the base in a liquid medium in which the ratio $[X^{k-}]:[A]$ is no greater than 1.6, wherein M is a metal, and wherein k>0.

2. The method of claim 1, wherein X=OH, and wherein $[A]:[OH^-]$ is no greater than 1.6.

3. The method of claim 2, wherein $[A]:[OH^-]$ is within the range of about 0.5 to 1.6.

4. The method of claim 2, wherein $[A]:[OH^-]$ is within the range of about 0.7 to about 1.5.

5. The method of claim 2, wherein $[A]:[OH^-]$ is within the range of about 0.8 to about 1.4.

6. The method of claim 2, wherein $[A]:[OH^-]$ is within the range of about 0.9 to about 1.3.

7. The method of claim 2, wherein $[A]:[OH^-]$ is within the range of about 1.0 to about 1.2.

8. The method of claim 1, wherein M is an alkali metal.

9. The method of claim 1, wherein the base is selected from the group consisting of LiOH, NaOH, KOH and CsOH.

10. The method of claim 9, wherein the base is NaOH.

11. The method of claim 9, wherein the base is KOH.

12. The method of claim 1, wherein k=1.

13. The method of claim 1, wherein A has the formula wherein L is a linking group, and wherein $R_1$ and $R_2$ are independently selected from the group consisting of substituted or unsubstituted alkyl, aryl or alkylaryl group.

14. The method of claim 13, wherein $R_1$ and $R_2$ are identical.

15. The method of claim 13, wherein L is a linking group having the structure —[CH$_2$]—, where n is an integer.

16. The method of claim 15, wherein n is in the range of 1 to about 50.

17. The method of claim 15, wherein n is in the range of 1 to about 20.

18. The method of claim 15, wherein n is in the range of 1 to about 10.

19. The method of claim 15, wherein n is in the range of 1 to 5.

20. The method of claim 14, wherein L contains at least one hetero atom selected from the group consisting of N, O and S.

21. The method of claim 14, wherein $R^2$ is selected from the group consisting of methyl, ethyl, propyl, and butyl groups.

22. The method of claim 13, wherein $R^2$ is an alkyl moiety having 1 to 20 carbon atoms.

23. The method of claim 13, wherein A is a diester, and wherein the step of reacting the compound with the base yields a monoester of the formula 24. The method of claim 1, wherein A is dimethyl malonate.

25. The method of claim 23, wherein B is monomethyl malonate.

26. The method of claim 1, wherein A is diethyl malonate.

27. The method of claim 26, wherein B is monoethyl malonate.

28. The method of claim 1, wherein A is dipropyl malonate.

29. The method of claim 28, wherein B is monopropyl malonate.

30. The method of claim 1, wherein A is dibutyl malonate.

31. The method of claim 30, wherein B is monobutyl malonate.

32. The method of claim 1, wherein the compound is reacted with the base at a temperature T, and wherein T<15° C.

33. The method of claim 1, wherein the compound is reacted with the base at a temperature T, and wherein T<10° C.

34. The method of claim 1, wherein the compound is reacted with the base at a temperature T, and wherein T<5° C.

35. The method of claim 1, wherein the compound is reacted with the base at a temperature T, and wherein −15° C.<T<15° C.

36. The method of claim 1, wherein the compound is reacted with the base at a temperature T, and wherein −10° C.<T<10° C.

37. The method of claim 1, wherein the compound is reacted with the base at a temperature T, and wherein −5° C.<T<5° C.

38. A method for hydrolyzing an ester, comprising:
providing a symmetric compound having first and second ester moieties; reacting the compound with a base to form a first product such that the ratio of the number of molar equivalents of base to the number of molar equivalents of the compound is no greater than 1.6; and
acidifying the first product to produce a second product.

39. The method of claim 38, wherein the compound is a linear diester.

40. The method of claim 39, wherein the reaction produces a half ester.

41. The method of claim 38, wherein the reaction is conducted in an aqueous medium.

42. The method of claim 38, wherein the reaction is conducted in a medium comprising water and a second material selected from the group consisting of THF, CH$_3$CN, CH$_2$Cl$_2$, methanol, ethanol, 1-propanol, 2-propanol, and DMSO.

43. The method of claim 42, wherein the second material is selected from the group consisting of THF and CH$_3$CN.

44. The method of claim 42, wherein the percent by volume of the second material, as measured by the volumes of the components of the reaction medium prior to mixing, is less than 7%.

45. The method of claim 42, wherein the percent by volume of the second material, as measured by the volumes of the components of the reaction medium prior to mixing, is less than about 5%.

46. The method of claim 42, wherein the percent by volume of the second material, as measured by the volumes of the components of the reaction medium prior to mixing, is less than about 3%.

47. The method of claim 42, wherein the percent by volume of the second material, as measured by the volumes of the components of the reaction medium prior to mixing, is essentially 100%.

48. A method for hydrolyzing an ester, comprising:
providing a compound having first and second ester moieties linked by an aromatic group;
reacting the compound with a base in an aqueous medium comprising greater than 93% water by volume to form a first product; and
acidifying the first product to produce a second product.

49. The method of claim 48, wherein the medium comprises greater than 95% water by volume.

50. The method of claim 48, wherein the medium comprises greater than 97% water by volume.

51. The method of claim 48, wherein the medium comprises essentially 100% water by volume.

52. The method of claim 48, wherein the compound is a linear diester, and wherein reacting the compound with a base produces a half ester.

53. The method of claim 48, wherein the compound is a cyclic diester, and wherein reacting the compound with a base produces a half ester.

54. The method of claim 48, wherein the ratio of the number of molar equivalents of base to the number of molar equivalents of the compound is no greater than 1.6.

55. The method of claim 48, wherein the compound is A, wherein the base has the formula $M_aX_b$, wherein X=OH, and wherein [A]:[OH$^-$] is within the range of about 0.5 to 1.6.

56. The method of claim 48, wherein the compound is A, wherein the base has the formula $M_aX_b$, wherein X=OH, and wherein [A]:[OH$^-$] is within the range of about 0.7 to 1.5.

57. The method of claim 48, wherein the base is selected from the group consisting of LiOH, NaOH, KOH and CsOH.

58. The method of claim 48, wherein the base is NaOH.

59. The method of claim 48, wherein the base is KOH.

60. The method of claim 48, wherein the compound has the formula wherein L is an aromatic linking group, and wherein $R_1$ and $R_2$ are independently selected from the group consisting of substituted or unsubstituted alkyl, aryl or alkylaryl group.

61. The method of claim 48, wherein $R_1$ and $R_2$ are identical.

62. The method of claim 61, wherein $R^2$ is selected from the group consisting of methyl, ethyl, propyl, and butyl groups.

63. The method of claim 61, wherein $R^2$ is an alkyl moiety having 1 to 20 carbon atoms.

64. The method of claim 48, wherein the compound is reacted with the base at a temperature T, and wherein T<15° C.

65. The method of claim 48, wherein the compound is reacted with the base at a temperature T, and wherein T<10° C.

66. The method of claim 48, wherein the compound is reacted with the base at a temperature T, and wherein T<5° C.

67. The method of claim 48, wherein the compound is reacted with the base at a temperature T, and wherein −15° C.<T<15° C.

68. The method of claim 48, wherein the compound is reacted with the base at a temperature T, and wherein −10° C.<T<10° C.

69. The method of claim 48, wherein the compound is reacted with the base at a temperature T, and wherein −5° C.<T<5° C.

* * * * *